United States Patent [19]

Koulbanis et al.

[11] 4,288,433

[45] Sep. 8, 1981

[54] COSMETIC COMPOSITIONS HAVING A SLIMMING ACTION

[75] Inventors: Constantin Koulbanis, Paris; Claude Bouillon, Eaubonne; Patrick Darmenton, Villejuif, all of France

[73] Assignee: L'Oreal, Paris, France

[21] Appl. No.: 78,513

[22] Filed: Sep. 24, 1979

Related U.S. Application Data

[62] Division of Ser. No. 849,128, Nov. 7, 1978, abandoned.

[30] Foreign Application Priority Data

Nov. 8, 1976 [LU] Luxembourg .......................... 76148

[51] Int. Cl.³ .................. A61K 31/625; A61K 31/52; A61K 31/22; A61K 31/465
[52] U.S. Cl. ............................ 424/232; 128/207.21; 424/253; 424/259; 424/264; 424/275; 424/311; 424/313; 424/330; 424/337; 424/359; 128/207.22
[58] Field of Search ................. 128/172, 172.1, 172.2, 128/156; 424/259, 359, 253, 275, 311, 313, 232, 264, 330, 337

[56] References Cited

U.S. PATENT DOCUMENTS

| Re. 29,256 | 6/1977 | Joullie et al. .......................... 424/311 |
| 3,671,643 | 6/1972 | Kalopissis ............................ 424/275 |
| 3,849,576 | 11/1974 | Kalopissis ............................ 424/330 |
| 3,879,560 | 4/1975 | Kalopissis ............................ 424/316 |
| 3,919,226 | 11/1975 | Thiel et al. ........................... 424/253 |
| 3,950,532 | 4/1976 | Bouillon et al. ..................... 424/275 |
| 3,976,781 | 8/1976 | Kalopissis ............................ 424/309 |
| 3,978,213 | 8/1976 | Lapinet et al. ....................... 424/253 |
| 4,002,671 | 1/1977 | Kalopissis ....................... 260/501.12 |
| 4,086,347 | 4/1978 | Friebe et al. ........................ 424/253 |
| 4,123,534 | 10/1978 | Credner et al. ..................... 424/253 |

OTHER PUBLICATIONS

Chem. Abst. 71, 120114(c) (1969)–Cuthbent et al.
Gazette Medicale de France–Paris, 79 (33) (1972)–pp. 5906–5908–Sors.

Primary Examiner—Douglas W. Robinson
Attorney, Agent, or Firm—Mason, Mason and Albright

[57] ABSTRACT

The invention provides compositions which have a slimming and anti-cellulitis action when applied to the body, topically with massage or using trans-cutaneous electrophoresis. The compositions contain, in combination, a thioether and a xanthine derivative.

6 Claims, No Drawings

COSMETIC COMPOSITIONS HAVING A SLIMMING ACTION

This application is a division of Ser. No. 849,128, filed Nov. 7, 1978 now abandoned.

The present invention relates to a cosmetic composition for the skin and especially a composition having a slimming and anti-cellulitis action.

It will be recalled that cellulitis is the local accumulation of fat and water which are confined in a matrix of more or less impervious cells. This matrix is made up of constituents of the basic matter and more especially proteoglycanes which are polymeric substances.

In order to release the fat and the water bonded to the polymeric substances which are responsible for the formation of the rolls of fat found on certain persons, it has been proposed to apply to the affected regions compositions based on enzymes which are capable of depolymerising the proteoglycanes. As the polymeric substances are mucopolysaccharides, these enzymes are therefore mucopolysaccharidases, more particularly hyaluronidase, thiomucase and α-mucase.

The purpose of these enzymes is therefore to split the long mucopolysaccharide chains into shorter chains with the release of water molecules. However, it has become apparent that their use poses problems which are difficult to surmount because, on the one hand, these enzymes have a limited lifetime, which renders their formulation difficult and their activity particularly uncertain, and, on the other hand, they are rather poorly tolerated by the skin and frequently cause severe irritations.

It has also been proposed to use phosphodiesterase inhibitors in order to prevent, or at least restrict the rate of, the degradation of cyclic AMP. In fact, phosphodiesterase destroys cyclic AMP by converting it into 5'-AMP so that it can not act as an lipolysis activator.

It is therefore important to inhibit the action of the phosphodiesterase in order to have a high level of cyclic AMP in the adipocytes with the aim of stimulating the lipolytic activity.

Among the different phosphodiesterase inhibitors which have been proposed, there may be mentioned in particular the xanthic bases, and more particularly theophylline, caffeine and theobromine. However, it has been shown that the results obtained with these inhibitors, taken by themselves or in association with the abovementioned enzymes, is not very satisfactory with regard to reducing cellulitis.

It has also been proposed to use certain water-soluble organic derivatives of silicon. However, the compositions based on these derivatives, and in particular those based on monomethyltrisilanol mannuronate, sold under the trade name of "ALGISIUM", have not made it possible to obtain appreciable reductions of cellulitis and rolls of fat.

We have now found, entirely surprisingly, according to the present invention, that it is possible to act on the cellulitis and achieve a slimming action by using a cosmetic composition containing certain sulphur-containing compounds in association with certain substituted xanthines.

In fact, the work which we have carried out makes it possible to demonstrate that, using this combination, remarkable results can be obtained both from the point of view of the slimming action and from the point of view of the anti-cellulitis action.

No explanation can currently be provided for the excellent activity observed. However, it is thought that these compositions may stimulate the activity of the cytochrome oxidases. In other words, these compositions may stimulate cellular respiration and oxidative metabolism.

The present invention provides a cosmetic composition for the skin having a slimming and anti-cellulitis action, this composition containing, in a suitable cosmetic vehicle:

(i) at least one sulphur-containing organic compound of the thioether type, and (ii) at least one xanthine derivative.

The sulphur-containing organic compound which is present in the compositions according to the invention is a thioether, preferably a linear thioether derived from cysteine, homocysteine or from cysteamine, or a cyclic thioether such as thiolane-3,4-diol or one of its oxidation products.

Suitable such sulphur-containing organic compounds include those described in U.S. Pat. Nos. 3,976,781, 3,849,576, 3,879,560, 4,002,671 and 3,950,532, the disclosure of which is hereby incorporated by reference.

Particularly significant results have been found when the sulphur-containing organic compound is S-carboxymethylcysteine, S-carboxymethylhomocysteine, thiolane-3,4-diol, thiolane-3,4-diol S-oxide, thiolane-3,4-diol S-dioxide, or an inorganic or organic salt of 2-benzylthioethylamine, especially the malate, salicylate, nicotinate, tartrate or 5-amino-3-thiahexanedioate.

In general, the sulphur-containing organic derivative is present in the composition at a concentration of from 0.1 to 5% by weight, preferably from 0.2 to 1.5%, by weight based on the total weight of the composition.

The xanthine derivative which can be used in the compositions according to the invention preferably corresponds to the following general formula:

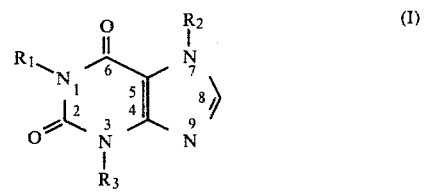

in which each of $R_1$ and $R_3$ independently represents a hydrogen atom, a linear or branched alkyl radical having up to 5 carbon atoms, an allyl radical, a propynyl radical or a cyclohexyl radical, with the proviso that $R_1$ and $R_3$ do not simultaneously represent a hydrogen atom, and $R_2$ represents a hydrogen, methyl, ethyl, hydroxymethyl or hydroxyethyl radical. These xanthines can be obtained using conventional processes.

Amongst the substituted xanthine, the following may be mentioned in particular: theophylline (or 1,3-dimethylxanthine), theobromine (or 3,7-dimethylxanthine), caffeine (or 1,3,7-trimethylxanthine), 3-butyl-1-methylxanthine, 3-isobutyl-1-methylxanthine, 1,3,7-triethylxanthine, 3-cyclohexyl-1-ethylxanthine, 3-ethyl-1-propynylxanthine and 3-ethyl-1-pentylxanthine.

This xanthine derivative is generally present in the composition at a concentration of from 0.1 to 2%, and preferably from 0.5 to 1% by weight based on the total weight of the composition.

The compositions according to the invention can be in various forms and especially in the form of aqueous solutions or aqueous-alcoholic solutions having an alcohol (ethanol or isopropanol) content of less than 20%, or in the form of emulsions, creams, gels or, if appropriate, aerosol foams.

Although the constituents of the compositions according to the invention are in themselves sufficient to produce excellent results which are clearly perceptible, it is also possible to introduce into the compositions various additional substances which have the effect of improving or accelerating the slimming or anti-cellulitis action.

Amongst these substances, the following may be mentioned in particular:

(1) Hydrosoluble organic compounds derived from monomethyltrisilanol, such as monomethyltrisilanol mannuronate, marketed by Messrs. EXYMOL under the name of "Algisium" (an aqueous solution containing 1% of monomethyltrisilanol mannuronate), or monomethyltrisilanol lactate, sold by the same Company under the name of "Lasilium" (an aqueous solution containing 1% of monomethyltrisilanol lactate).

According to the present invention, these compounds are preferably present in the compositions at a concentration of from 0.01 to 0.95%, and preferably from 0.1 to 0.6%, by weight (expressed as active material).

(2) Enzymes of the mucopolysaccharidase type, and especially thiomucase, hyaluronidase or α-mucase.

In a preferred embodiment according to the invention, the hyaluronidase known under the trade name of "HYALASE" is more particularly used. This is a lyophilised extract of bull testicles in the form of a deep creamy yellow amorphous powder, of which the solubility in water is of the order of 5 g/liter.

In the compositions according to the invention, the enzyme of the mucopolysaccharidase type is preferably present in an amount sufficient for the composition to contain from 5 to 50,000 TR units (turbidity-reducing units).

(3) Natural extracts, such as the extract of *Centella Asiatica*.

According to this embodiment, the concentration of extracts is preferably from 0.01 to 0.1% by weight based on to the total weight of the composition.

The compositions according to the invention can of course also contain other ingredients, in particular preservatives, perfumes or dyestuffs.

The present invention also relates to a process for the treatment of the skin to combat cellulitis and rolls of fat, this process consisting in applying, with massaging, a sufficient amount of a composition according to the invention to the parts of the body to be treated.

This massage process is more particularly used when the compositions are in the form of emulsions, creams, gels or aerosol foams.

The duration of the treatment naturally varies, but it generally gives completely satisfactory results it is is carried out for a period of two to eight weeks at a rate of one application per day.

The present invention also relates to a particular process for the treatment of cellulitis using compositions according to the invention which are in the form of solutions, this process involving the use of the so-called transcutaneous electrophoresis technique, which is also called the ionisation or iontophoresis technique. It will be recalled that this technique of treatment consists in causing an ionisable substance to migrate, by means of a low intensity galvanic current, across the skin and the surface tissues of the dermis, in order to impregnate the subdermal connective zone to be treated. Various types of apparatus, and especially the apparatus called "Prodion", can be used in order to carry out this treatment.

According to this process, the electrodes are covered with a layer of, say, cotton wool, and the treating electrode, which is soaked with the composition according to the invention, is applied to the part of the body to be treated, the opposite electrode being applied to another part of the body.

If the product to be ionised is electronegative, the treating electrode, which carries the product according to the invention, is connected to the negative pole of the apparatus. Instead, it is possible to soak both electrodes with the product according to the invention, and to reverse the electrode connections during the treatment. This embodiment is of particular value when the products to be ionised are at the same time electro-negative and electro-positive.

In general terms, the duration of the ionisation operations is of the order of 10 to 30 minutes, and more generally about 20 minutes. The intensity of the current is generally from 4 to 6 milliamperes depending on the cutaneous reaction of the persons to be treated.

This treatment is preferably carried out at a rate of three ionisation operations per week for a duration of 4 to 8 weeks.

Other methods of treatment can of course also be employed, especially those using injection or multiinjections. The injections are preferably performed subcutaneously or intradermally in the areas to be treated, so that a better action is obtained. It is also possible to envisage treatment by spraying under pressure.

The following Examples further illustrate the present invention.

EXAMPLE I

An anti-cellulitis solution is prepared, according to the invention, by mixing the following ingredients:

| | | |
|---|---|---|
| caffeine | 1 | g |
| S-carboxymethylcysteine | 1 | g |
| triethanolamine q.s.p. pH 6.5 | | |
| methyl p-hydroxybenzoate | 0.3 | g |
| water q.s.p. | 100 | g |

The application of this solution in accordance with the process of transcutaneous electrophoresis, at a rate of three applications per week for 4 to 6 weeks, makes it possible to obtain excellent results for the reduction of cellulitis on the hips and the thighs.

EXAMPLE II

An anti-cellulitis solution is prepared, according to the invention, by mixing the following ingredients:

| | | |
|---|---|---|
| theophylline | 0.5 | g |
| S-carboxymethylcysteine | 1 | g |
| potassium hydroxide q.s.p. pH 6.5 | | |
| propyl p-hydroxybenzoate | 0.3 | g |
| water q.s.p. | 100 | g |

The application of this solution using the process of transcutaneous electrophoresis makes it possible to achieve an excellent anti-cellulitis effect after a treatment of 4 to 5 weeks at a rate of three applications per week.

EXAMPLES III to VI

Anti-cellulitis solutions are prepared, according to the invention, by mixing the following ingredients:

EXAMPLE III

| | | |
|---|---|---|
| caffeine | 1 | g |
| 2-benzylthioethylammonium malate | 1 | g |
| methyl p-hydroxybenzoate | 0.1 | g |
| propyl p-hydroxybenzoate | 0.1 | g |
| water q.s.p. | 100 | g |

In this example, the 2-benzylthioethylammonium malate can be advantageously replaced by the same amount of 2-benzylthioethylammonium salicylate, nicotinate or tartrate.

EXAMPLE IV

| | | |
|---|---|---|
| caffeine | 0.8 | g |
| thiolane-3,4-diol S-dioxide | 0.8 | g |
| propyl p-hydroxybenzoate | 0.3 | g |
| Hyalase 10,000 TR units | | |
| monomethyltrisilanol mannuronate (1% strength solution in water) q.s.p. | 100 | g |

EXAMPLE V

| | | |
|---|---|---|
| caffeine | 1 | g |
| S-carboxymethylcysteine | 1 | g |
| extract of *CENTELLA ASIATICA* | 0.1 | g |
| propylene glycol | 10 | g |
| ethanol | 10 | g |
| triethanolamine q.s.p. pH 6.5 | | |
| allantoin | 0.1 | g |
| methyl p-hydroxybenzoate | 0.2 | g |
| propyl p-hydroxybenzoate | 0.1 | g |
| water q.s.p | 100 | g |

EXAMPLE VI

| | | |
|---|---|---|
| caffeine | 1 | g |
| 2-benzylthioethylammonium 5-amino-3-thiahexanedioate | 1.5 | g |
| propyl p-hydroxybenzoate | 0.3 | g |
| monomethyltrisilanol lactate (1% strength solution in water) q.s.p. | 100 | g |

On treatment by transcutaneous electrophoresis using these solutions 4 times per week for 3 or 4 weeks, an excellent result is found for the reduction of cellulitis on the thighs, the hips and the knees.

EXAMPLE VII

A slimming cream is prepared, according to the invention, by mixing the following ingredients:

| | | |
|---|---|---|
| stearic acid (triple-pressed) | 3 | g |
| isopropyl myristate | 5 | g |
| cetyl alcohol | 3 | g |
| glycerol monostearate | 3 | g |
| polyoxyethyleneated sorbitan monooleate | 3 | g |
| vaseline oil | 5 | g |
| monopropylene glycol | 4 | g |
| sorbitol | 3 | g |
| methyl p-hydroxybenzoate | 0.3 | g |

| -continued | | |
|---|---|---|
| S-carboxymethylcysteine | 1 | g |
| 3-isobutyl-1-methylxanthine | 1 | g |
| triethanolamine q.s.p. pH 6.5 | | |
| perfume | 0.3 | g |
| sterile dimineralised water q.s.p. | 100 | g |

This cream, applied by massage regularly every day to the hips and the thighs, makes it possible to achieve a reduction of rolls of fat after a treatment of 4 to 5 weeks.

In this example, the 3-isobutyl-1-methylxanthine can be advantageously replaced by the same amount of one of the following compounds: 3-butyl-1-methylxanthine, 3-ethyl-1-pentylxanthine and 1,3,7-triethylxanthine.

We claim:

1. A method for the treatment of cellulitis which comprises massaging the part of the body to be treated with a therapeutically effective amount of a composition containing in a suitable vehicle:
    (1) 0.1 to 1.5% by weight of a thioether selected from the group consisting of: S-carboxymethylcysteine, S-carboxymethylhomocysteine, thiolane-3,4-diol, thiolane-3,4-diol S-oxide, thiolane-3,4-diol S-dioxide and the malate, salicylate, nicotinate, tartrate or 5-amino-3-thiahexanedioate of 2-benzylthioethylamine, and
    (2) 0.1 to 2% by weight of a xanthine derivative having the formula:

$$\begin{array}{c} R_1-N \\ \diagdown \\ N \end{array} \begin{array}{c} O \\ \| \\ \end{array} \begin{array}{c} R_2 \\ | \\ N \\ \diagup \\ N \end{array}$$

in which each of $R_1$ and $R_3$ independently represents a hydrogen atom, a linear or branched alkyl radical having 1 to 5 carbon atoms, an allyl radical, a propynyl radical or a cyclohexyl radical with the proviso that $R_1$ and $R_3$ do not simultaneously represent a hydrogen atom and $R_2$ represents hydrogen, a methyl, ethyl, hydroxymethyl or hydroxyethyl radical.

2. The process of claim 1 in which said treatment is carried out once a day for 2 to 8 weeks.

3. The process of claim 1 in which said xanthine derivative is selected from the group consisting of theophylline, theobromine, caffeine, 3-butyl-1-methylxanthine, 3-isobutyl-1-methylxanthine, 1,3,7-triethylxanthine, 3-cyclohexyl-1-ethylxanthine, 3-ethyl-1-propynylxanthine and 3-ethyl-1-pentylxanthine.

4. A method for the treatment of cellulitis which comprises treating the skin, using the transcutaneous electrophoresis technique, with a therapeutically effective amount of an aqueous solution containing:
    (1) 0.1 to 1.5% by weight of a thioether selected from the group consisting of: S-carboxymethylcysteine, S-carboxymethylhomocysteine, thiolane-3,4-diol, thiolane-3,4-diol S-oxide, thiolane-3,4-diol S-dioxide and the malate, salicylate, nicotinate, tartrate or 5-amino-3-thiahexanedioate of 2-benzylthioethylamine, and
    (2) 0.1 to 2% by weight of a xanthine derivative having the formula:

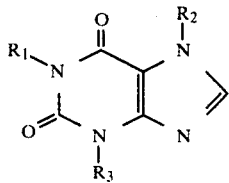

in which each of $R_1$ and $R_3$ independently represents a hydrogen atom, a linear or branched alkyl radical having 1 to 5 carbon atoms, an allyl radical, a propynyl radical or a cyclohexyl radical with the proviso that $R_1$ and $R_3$ do not simultaneously represent a hydrogen atom and $R_2$ represents hydrogen, a methyl, ethyl, hydroxymethyl or hydroxyethyl radical.

5. The process of claim 4 in which said treatment is carried out for 4 to 8 weeks at a rate of three ionisations per week.

6. The process of claim 4 in which said xanthine derivative is selected from the group consisting of theophylline, theobromine, caffeine, 3-butyl-1-methylxanthine, 3-isobutyl-1-methylxanthine, 1,3,7-triethylxanthine, 3-cyclohexyl-1-ethylxanthine, 3-ethyl-1-propynylxanthine and 3-ethyl-1-pentylxanthine.

* * * * *